US00PP17875P3

(12) United States Plant Patent
Gargiulo

(10) Patent No.: US PP17,875 P3
(45) Date of Patent: Jul. 24, 2007

(54) GRAPEVINE DENOMINATED 'BLACK GLOBE'

(50) Latin Name: *Vitis vinifera*
Varietal Denomination: Black Globe

(75) Inventor: Angel Antonio Gargiulo, San Rafael (AR)

(73) Assignee: M. Caratan, Inc., Delano, CA (US)

( * ) Notice: Subject to any disclaimer, the term of this patent is extended or adjusted under 35 U.S.C. 154(b) by 0 days.

(21) Appl. No.: 10/354,313

(22) Filed: Jan. 29, 2003

(65) Prior Publication Data

US 2006/0206971 P1 Sep. 14, 2006

(51) Int. Cl.
*A01H 5/00* (2006.01)

(52) U.S. Cl. ..... Plt./205

(58) Field of Classification Search ..... Plt./205
See application file for complete search history.

*Primary Examiner*—Kent Bell
(74) *Attorney, Agent, or Firm*—Jondle & Associates P.C.

(57) ABSTRACT

A new and distinct variety of grapevine which is characterized by producing a large, high quality, seeded table grape which has a dark blue to nearly black skin coloration and is ripe for commercial harvesting and shipment approximately early to mid-September near Delano in the San Joaquin Valley of central California is disclosed.

1 Drawing Sheet

Genus and species: *Vitis vinifera.*
Variety denomination: 'Black Globe'.

BACKGROUND OF THE INVENTION

The present invention relates to a new and distinct variety of grapevine, which will hereinafter be denominated varietally as the 'Black Globe' grapevine, and, more particularly, to a grapevine which produces large, high quality, dark blue to nearly black fruit, which are mature for commercial harvesting and shipment in approximately early to mid-September near Delano in the San Joaquin Valley of central California.

The grapevine of the subject invention was discovered by the inventor as the result of a breeding program carried out under his direction in 1989 in Delano, Calif. by cross pollination between the 'Red Globe' grapevine and the 'Fantasy' grapevine. The instant grapevine was first asexually reproduced in 1993 in Delano, Calif. under the direction of the inventor by grafting budwood of the new variety onto three-year-old 'Salt Creek' grapevine rootstock. The observations and measurements hereof were made during the 1994 growing season, at the same location near Delano in the San Joaquin Valley of central California, and in successive growing seasons thereafter. It has been found to retain its distinctive characteristics through successive asexual propagations.

SUMMARY OF THE INVENTION

The grapevine denominated 'Black Globe' is characterized by producing a large, high quality, seeded table grape which has a dark blue to nearly black skin coloration and is ripe for commercial harvesting and shipment approximately early to mid-September near Delano in the San Joaquin Valley of central California. This ripening date is from several days to a week in advance of the 'Emperor' grapevine. The fruit of the 'Black Globe' grapevine is darker in skin coloration than that of the 'Emperor' grapevine, particularly in low intensity growing situations, and has a substantially larger berry size. The fruit of 'Black Globe' is somewhat larger in cluster size than that of the 'Emperor' grapevine.

BRIEF DESCRIPTION OF THE DRAWING

The drawing is a color photograph of typical portions of the 'Black Globe' grapevine including four clusters of fruit thereof; two whole berries disposed in side elevation; two berries each individually sectioned along a plane transverse to the longitudinal axis thereof; one berry sectioned along a plane parallel to the longitudinal axis and laid open to expose the flesh and seeds thereof; a scale against which to register the size of the portions; and characteristic canes, tendrils and foliage, all of the new variety. The plant parts in the photograph were taken from a seven-year-old grapevine grown under field conditions in Delano, Calif.

DETAILED BOTANICAL DESCRIPTION

Referring more specifically to the botanical details of this new and distinct variety of grapevine, the following has been observed under the ecological conditions prevailing in the vineyard of origin which is located near Delano in the San Joaquin Valley of central California. The plant history was taken on seven-year-old grapevines grown under field conditions in Delano, Calif. All major color code designations are by reference to the *Dictionary of Color,* by Maerz and Paul, First Edition, published in 1930. Common color names are also occasionally employed.

Vine:
Generally: Size — Large.

*Vigor.*—Very vigorous, more vigorous than either the 'Thompson Seedless' or 'Flame Seedless' grapevine cultivars. The test grapevines of the new variety are planted in rows 3.7 meters apart with the grapevines within each row planted with a spacing of about 2.1 meters. The vine canopy extends from 0.9 meters to 1.1 meters out into the row.

*Productivity.*—Medium. The grapevines are slightly more productive than the 'Flame Seedless' grapevine and about equal to the 'Thompson Seedless' grapevine. The test vines have been trained in a cane pruned system so that bunch counts are maximized.

Trunk: Size — Diameter ranges from 64 mm (2.56 inches) to 76 mm (3.04 inches at 25 cm (9.75 inches) above the ground level.

*Surface texture.*—Somewhat grooved with a shaggy surface.

*Color.*—Bark — Brownish-grey (15-A-7 Soapstone) to brownish-copper (14-C-12 Tortoise Brown).

*Canes.*—Thickness — Average to above average, depending on light exposure and the height in the canopy. The canes range from 13 mm (0.52 inches) to 16 mm (0.64 inches) in diameter.

*Mature canes.*—Surface — Finely striated with low, somewhat irregular striations.

*Mature canes.*—Color — Copper Brown (14-B-11) to Tanbark Brown (14-B-8).

*Internodes.*—Length — Variable, with a joint frequency from 63 mm (2.52 inches) to 152 mm (6.08 inches).

*Woody shoots.*—Shape — Varies from nearly circular to elliptic in cross section.

*Tendrils.*—Generally — Medium in thickness and moderately long.

*Tendrils.*—Length — 15.0 cm (6.0 inches) to 18.0 cm (7.2 inches).

*Tendrils.*—Location — Discontinuous.

*Tendrils.*—Form — Variable, most frequently trifid in form, with occasional bifid types present.

*Tendrils.*—Color — Bronze-rust (13-L-5).

*Growing tip.*—Tip indument is slightly pubescent, with short, fine pubescence. Color of the expanding shoot tip is a bronze-rust (13-L-6) to (13-K-7), with a light amount of anthocyanic intensity.

Leaves:

*Size.*—Generally — Medium to large.

*Leaf blade length.*—Mature Leaf — Ranges from 132.0 mm (5.28 inches) to 160.0 mm (6.40 inches), measured from the petiolar junction to the apex of the center lobe.

*Texture.*—Upper Surface — Smooth.

*Texture.*—Lower Surface — Smooth.

*Form.*—Pentagonal.

*Color.*—Upwardly disposed surface — Dark green (23-L-7) with very slight reddish anthocyanic pigmentation present primarily on the upper midvein of the most mature and the most exposed leaves.

*Color.*—Downwardly disposed surface — Light grey-green (21-H-6).

*Color.*—Leaf Vein — Pale green (17-J-4).

*Petiole.*—Length — 110.0 mm (4.40 inches) to 142.0 mm (5.68 inches).

*Petiole.*—Thickness — 2.5 mm (0.10 inches) to 3.0 mm (0.12 inches).

*Petiole.*—Color — Light green (18-I-5) to slightly darker green (8-I-6), often with a light rose (3-D-2) to a dark maroon (4-E-5 Solferino) anthocyanic coloration on the petiole, which is more distinct on the basal portion of the petiole.

*Petiole sinus.*—Form — "U" shaped, open and occasionally toothed on the sinus margin. The upper leaf sinuses are usually closed, with the lobes overlapping. The bases of the upper leaf sinuses are usually "V" shaped.

*Lobes.*—Five lobes with broad, serrate margins. The sides of the margin serrations range from straight to slightly convex. Serrations are large from 5 mm (0.2 inches) to 10 mm (0.4 inches) in length. Lobe apices are acute in form.

Flowers:

*Date of full bloom.*—May 16 in 1995. Approximately the same bloom timing as that of the 'Flame Seedless' grapevine cultivar and from 3 to 4 days ahead of the 'Thompson Seedless' grapevine cultivar.

*Amount of pollen.*—Abundant.

*Floral cluster form.*—The floral cluster is moderately narrow and tapering. The 1$^{st}$ floral cluster occurs on the 3$^{rd}$ to 5$^{th}$ joint, most frequently on the 4$^{th}$ joint. Cluster frequency is average in number. At bloom, the clusters range in length from 17 cm (6.8 inches) to 25 cm (10.0 inches) from the base of the peduncle to the tendril, and from 26 mm (1.04 inches) to 35 mm (1.4 inches) from the tendril to the first rachis branch. Overall floral cluster size (minus the peduncle) ranges from 11.5 cm (4.49 inches) to 15.7 cm (6.12 inches) in length, and from 3.6 cm (1.4 inches) to 7.3 cm (2.85 inches) in width. The flowers are hermaphroditic, with upright stamens and average size anthers. Pollen production is abundant. The floral calyptra separates completely from the flower base. Length of the bloom period is normal, approximately ten days in duration.

*Floral cluster coloration.*—The pedicel color at bloom is a medium green, from (20-K-4) to (20-K-5). Calyptra color is a medium green (20-K-6).

*Stamen number.*—5.

*Stamen color.*—Light Yellow (17-G-1).

*Pistil number.*—1.

*Pistil color.*—Light Yellow-Green (17-K-6).

*Pistil length.*—1–2 mm.

*Petal color.*—Medium Green (20-K-6).

*Sepal color.*—Medium Green (20-K-6).

*Sepal number.*—5 (at times coalesced together).

Fruit:

Maturity when described: Ripe for commercial harvesting and shipment approximately early to mid-September near Delano in the San Joaquin Valley of central California, from several days to a week earlier than the 'Emperor' grapevine. The date of maturity for any grape cultivar can vary from season to season, depending on the accumulation of heat units during the growing season, thereby producing an "early" or "late" year. In 1994, the beginning of harvest was on the 20$^{th}$ of September at the Delano test planting, with completion of harvest by Oct. 1, 1994. During the 1997 harvest season, one of the earliest seasons on record, onset of harvest was on August 15, with completion of harvest by the 9$^{th}$ of September. A more normal (or average) year occurred in 1996 with onset of harvest on September 1$^{st}$ and completion of harvest by September 20$^{th}$.

*Seeds.*—1 to 3 per berry.

Size: Cluster — Generally — Medium to large. Bunch length ranges from 20 cm (7.8 inches) to 28 cm (10.92 inches), without the peduncle. Bunch width ranges from 13 cm (5.07 inches) to 18 cm (7.02 inches).

*Mature cluster weight.*—2–3 lbs.

*Mature cluster pH.*—4.1.

*Mature cluster soluble solids.*—18–20 degrees brix.

*Compactness.*—Moderately loose, with a moderate number of visible pedicels.

*Cluster.*—Form — Narrow and tapering.

*Brush length.*—7–8 mm.

*Berry.*—Size — Large.

*Berry.*—Form — Obovate, at times elliptic in the lateral aspect.

*Berry.*—Size — Dimensions Longitudinal Axis — 26.0 mm (1.04 inches) to 38.0 mm (1.52 inches). Highly uniform.

*Berry.*—Size — Diameter Axis — 22.0 mm (0.88 inches) to 27.0 mm (1.08 inches).

*Berry.*—Numbers — 65 to 85 per medium cluster to 125 to 138 per large cluster.

*Form.*—In cross-section is most frequently globose.

*Peduncle.*—Varies from 21 mm (0.84 inches) to 50 mm (2.0 inches) in length and from 3.5 mm (0.14 inches) to 7.0 mm (0.28 inches) in thickness measured at mid-peduncle.

*Peduncle.*—Color — Medium green (21-K-4 Rainette Green).

*Berry pedicel.*—The pedicel length is medium, ranging from 10 mm (0.4 inches) to 18 mm (0.72 inches). Pedicel thickness varies from 1.5 mm (0.06 inches) to 2.5 mm (0.1 inches), measured at mid-pedicel. Pedicel color is green (20-K-4). Pedicel attachment is very good, with no shatter occurring even at full maturity.

Skin: Texture — Crisp and firm.

*Color.*—Variable. Purple maroon (7-H-5 Aubusson) to blue-purple (48-H-9). The darkest coloration is a blue-purple (48-H-9), with lighter shades ranging to a purple-maroon (7-H-5 Aubusson). The lighter shading is most frequently found at the stem end of the berry. Blue to purple color covers from 95 to 100 percent of the total skin surface. Occasionally, on the lightest colored berries, a small amount (5%) of green ground color can be present next to the stem (13-J-1). Usually, most berries on the cluster are fully colored. Only the most heavily shaded berries or the most interior berries retain any green ground color. A light, uniform, greyish colored bloom usually covers the entire berry surface. The bunches usually color well, even in low light intensity under dense, shaded canopies.

Flesh: Flesh Color — Variable. Clear to light greenish-white (18-D-2 Sea Foam Green). The greenish color intensity is usually more intense at the center of the berry. At times the berry flesh is pinkish in color (5-B-1), again, more intense in color at the center of the berry.

*Flavor.*—Sweet, mild and well balanced.

*Aroma.*—Absent to very light.

*Secondary bunches.*—The secondary bunches found on this new variety are relatively few in number and small in size. Berry shape and berry color are similar to those berries found in primary bunches. Bunch form is irregular. Bunch width ranges from 55 mm (2.2 inches) to 83 mm (3.32 inches) and bunch length ranges from 45 mm (1.8 inches) to 95 mm (3.8 inches). Berry count in the secondary bunches varies substantially, from 3 to 18 berries.

*Cold hardiness.*—5–10° F.

*Disease resistance.*—None.

*Pest resistance.*—None.

Use: High quality, seeded dark blue to nearly black table grape ideally suited for fresh consumption.

Although the new variety of grapevine possesses the described characteristics noted above as a result of the growing conditions prevailing near Delano in the central part of the San Joaquin Valley of California, it is to be understood that variations of the usual magnitude and characteristics incident to changes in growing conditions, irrigation, fertilization, pruning, pest control, climatic variations and the like are to be expected.

COMPARISON WITH PARENTAL CULTIVARS

'Black Globe' differs from the parental cultivar 'Red Globe' (unpatented) by having black-skinned fruit and by having a higher brix level at maturity than 'Red Globe'. 'Black Globe' differs from the parental cultivar 'Fantasy' (unpatented) by having seeds and by having fuller and heavier fruit clusters than 'Fantasy'.

I claim:

1. A new and distinct variety of grapevine plant as shown and described herein.

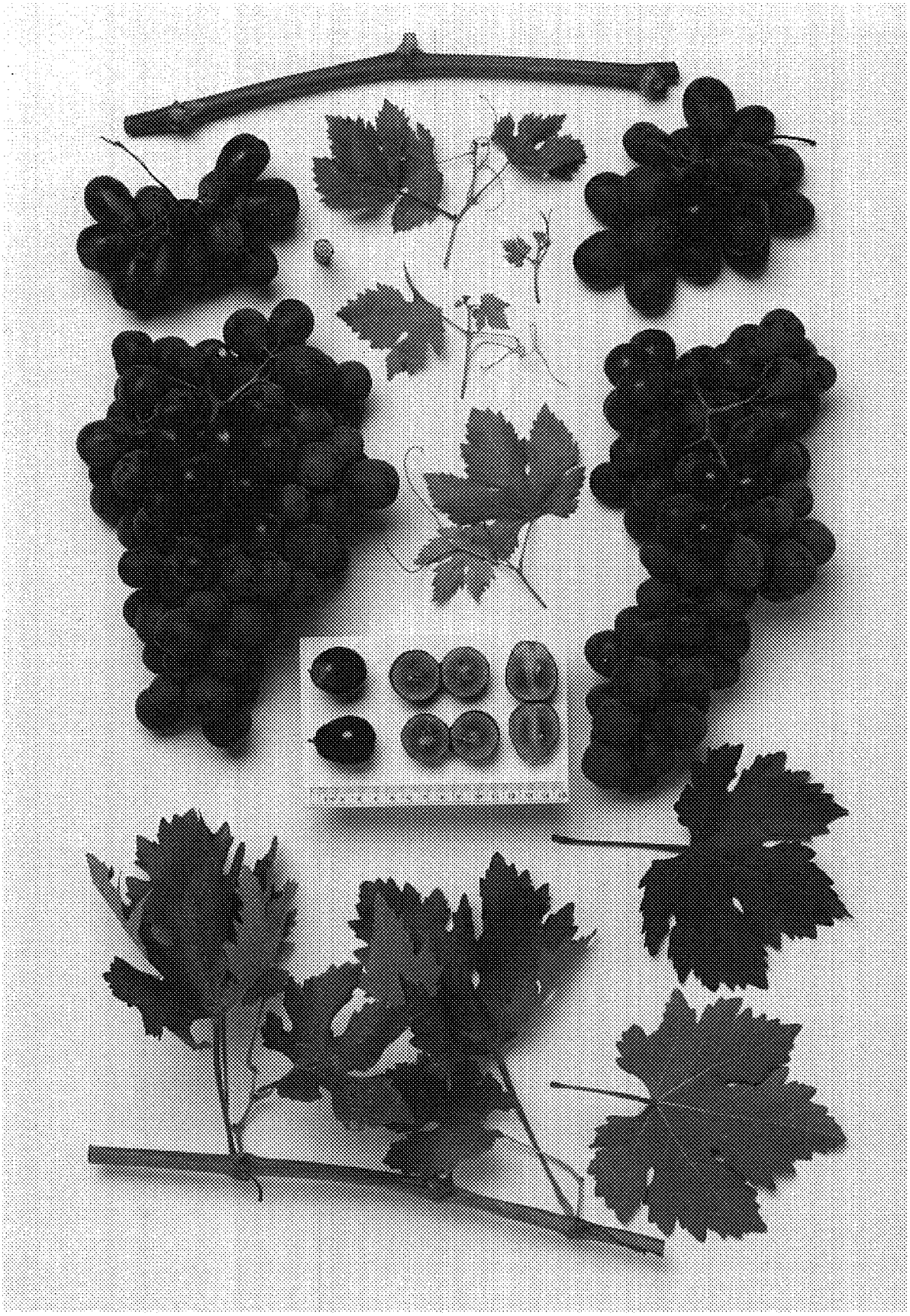

* * * * *